United States Patent
Tsai

(10) Patent No.: US 6,186,944 B1
(45) Date of Patent: Feb. 13, 2001

(54) MEDICAL INSPECTION DEVICE

(76) Inventor: Jory Tsai, 14 Orchard Dr., Hudson, MA (US) 01749

( * ) Notice: Under 35 U.S.C. 154(b), the term of this patent shall be extended for 0 days.

(21) Appl. No.: 09/199,963

(22) Filed: Nov. 25, 1998

(51) Int. Cl.[7] .................................................. A61B 1/227
(52) U.S. Cl. ......................... 600/200; 600/109; 600/130; 600/167; 600/179
(58) Field of Search ..................... 600/109, 129, 600/130, 131, 167, 179, 199, 200; 433/29; 348/65, 66

(56) References Cited

U.S. PATENT DOCUMENTS

| | | | |
|---|---|---|---|
| 4,604,992 | * | 8/1986 | Sato ....................................... 600/108 |
| 4,633,304 | * | 12/1986 | Nagasaki ................................ 348/69 |
| 4,742,819 | * | 5/1988 | George .................................. 600/109 |
| 4,884,133 | * | 11/1989 | Kanno et al. ........................... 348/68 |
| 5,363,838 | | 11/1994 | George . |
| 5,373,317 | * | 12/1994 | Salvatti et al. .......................... 348/65 |
| 5,527,261 | | 6/1996 | Monroe et al. . |
| 5,634,790 | | 6/1997 | Pathmanabhan et al. . |
| 5,658,235 | | 8/1997 | Priest et al. . |
| 5,701,155 | | 12/1997 | Wood et al. . |
| 5,701,904 | | 12/1997 | Simmons et al. . |
| 5,702,345 | | 12/1997 | Wood et al. . |
| 5,733,029 | * | 3/1998 | Monroe ................................ 362/572 |
| 5,751,341 | | 5/1998 | Chaleki et al. . |
| 5,762,605 | | 6/1998 | Cane et al. . |
| 5,873,814 | * | 2/1999 | Adair ................................... 600/109 |
| 5,879,289 | * | 3/1999 | Yarush et al. ........................ 600/179 |
| 5,885,214 | * | 3/1999 | Monroe et al. ...................... 600/407 |
| 5,919,130 | * | 7/1999 | Monroe et al. ...................... 600/200 |
| 6,106,457 | | 8/2000 | Perkins et al. . |

* cited by examiner

Primary Examiner—John P. Leubecker
(74) Attorney, Agent, or Firm—Sampson & Associates, P.C.

(57) ABSTRACT

The present invention includes a dental/medical instrument for use in diagnostic and related patient inspection/examination. The device includes a body including an integral speculum with a video image capture device or camera, a power supply and a video display. These components, in addition to user actuatable controls, are disposed integrally with the body. The body is adapted for convenient engagement and manipulation by a user's hand to provide a unitary, hand-held device capable of illuminating and capturing an image of a patient, and displaying the image.

23 Claims, 4 Drawing Sheets

MEDICAL INSPECTION DEVICE

BACKGROUND OF THE INVENTION

1. Field of the Invention

The present invention relates to medical and dental optical diagnostic instruments, and more particularly to an integrated hand held viewing scope and display for use as an otoscope, ophthalmoscope, larynx illumination, nasopharynx illuminator, dermatologic magnifier and anoscope.

2. Background Information

Various hand held instruments for use by a physician or dentist during examination of a patient have been known in the art for many years. Such hand held instruments include the otoscope for examination of the ear, ophthalmoscope for examination of the eye, larynx illuminator (throat), nasal pharynx illuminator (nasal passages), dermatologic magnifier (skin) and anoscope (lower G.I. tract).

Also, in the prior art, it has been known to employ miniature or micro-video cameras in connection with various surgical procedures which occur in the operating room. Examples of such video cameras are known as remote head color CCD cameras. These cameras typically employ an array of semiconductive chips using a technology known as charge coupled diode sensors. Such micro-cameras are capable of yielding more than 500 lines of resolution per axis, resulting from the use of 400,000 or more pixels. Use of such micro-video cameras and related equipment, such as endocouplers, have been known for some time in connection with certain types of surgery and, particularly, surgery conducted through the use of small incisions in the body wall in videoendoscopy procedures. Such procedures have become increasingly commonplace in connection with procedures upon the gall bladder, appendix, intestine, etc., where the problem is of an internal nature.

In addition to relatively widespread use of such micro-video technology in the operating room, which includes the display of a procedure upon separate monitors, this technology has also been utilized in the dentist's or physician's office in the context of otherwise routine examination and diagnosis. An example of an instrument incorporating this technology is shown, for example, in U.S. Pat. No. 5,762,605, issued to Cane et al. This device discloses a hand held optical diagnostic instrument including a CCD sensor and an external light source. The instrument is coupled to a discreet monitor which may permit both patient and physician to observe an image of the examination. Moreover, devices of this type may be utilized to produce a video record of such an examination and/or provide either a video tape of the examination or selected print frames thereof.

Such devices may also be used to provide a video link to a satellite or other communications means from a video interface of the system. This may enable consultants to be utilized either in real time, or in a batch mode, to provide "second opinions" to the examining medical personel or paramedic who may be located in a geographically remote region and/or may possess limited skills in the specialty to which the examination relates. Such activity has become known as telemedicine.

A disadvantage of such devices, however, is that they tend to be awkward to use, as such instruments tend to be difficult for the examining physician to hold, to manipulate and to obtain the necessary views for the examination while simultaneously viewing the image on the remote monitor. This is due to the need for the examining care provider to manipulate the instrument relative to the patient, while looking away from the patient to the monitor. Thus, while many prior art instruments may be designed to facilitate manipulation by the user, the ergonomics of such devices tends to divert the users attention away from the patient during examination, which may result in discomfort to the patient due to errant manipulation of the instrument. This drawback may be particularly problematic with respect to new users, or those with minimal training in the use of such instruments.

Thus, a need exists for an ergonomically improved hand-held dental/medical instrument which enables a user to simultaneously observe both the patient and the instrument while viewing an image captured thereby.

SUMMARY OF THE INVENTION

According to the present invention, a dental/medical instrument includes a body adapted for engagement by a user's hand, a speculum integrally disposed within the body, an image capture device, a light source and a video display. The image capture device, light source and video display are disposed integrally within the body.

In another aspect of the present invention, a dental/medical instrument includes a body adapted for engagement by a user's hand, a speculum integrally disposed within the body, and an image capture device disposed integrally within the body, the image capture device having a central optical axis. A light source is also disposed integrally within the body, the light source being adapted to emit light along at least one light emission axis disposed substantially parallel to the central optical axis. A video display is disposed integrally with the body and is coupled with the video capture device to display an image captured thereby.

DETAILED DESCRIPTION OF THE PREFERRED EMBODIMENTS

Figure 1:
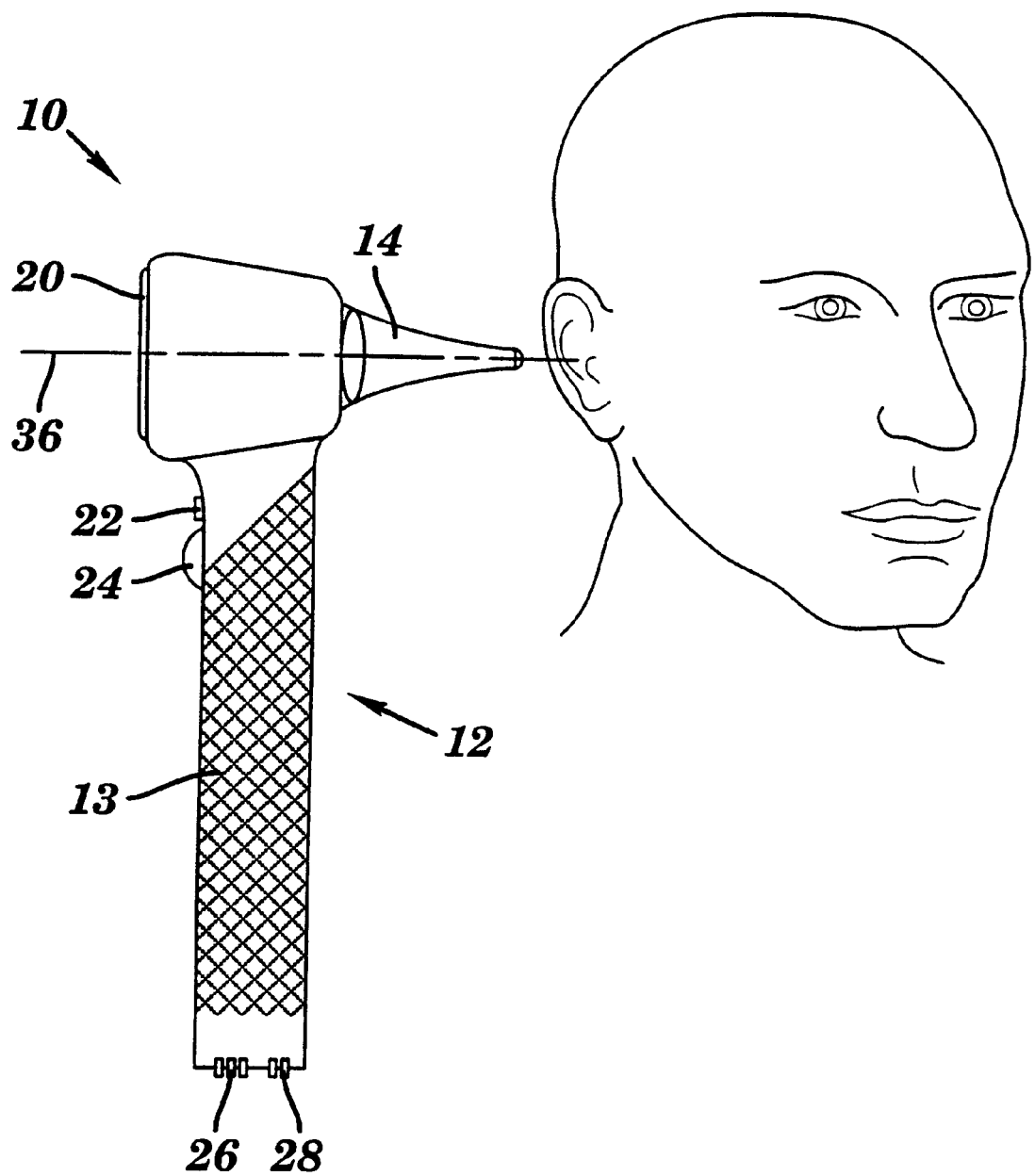
FIG. 1 is a partially perspective elevational view of a dental/medical instrument of the present invention in use relative to a patient.
Figure 2:
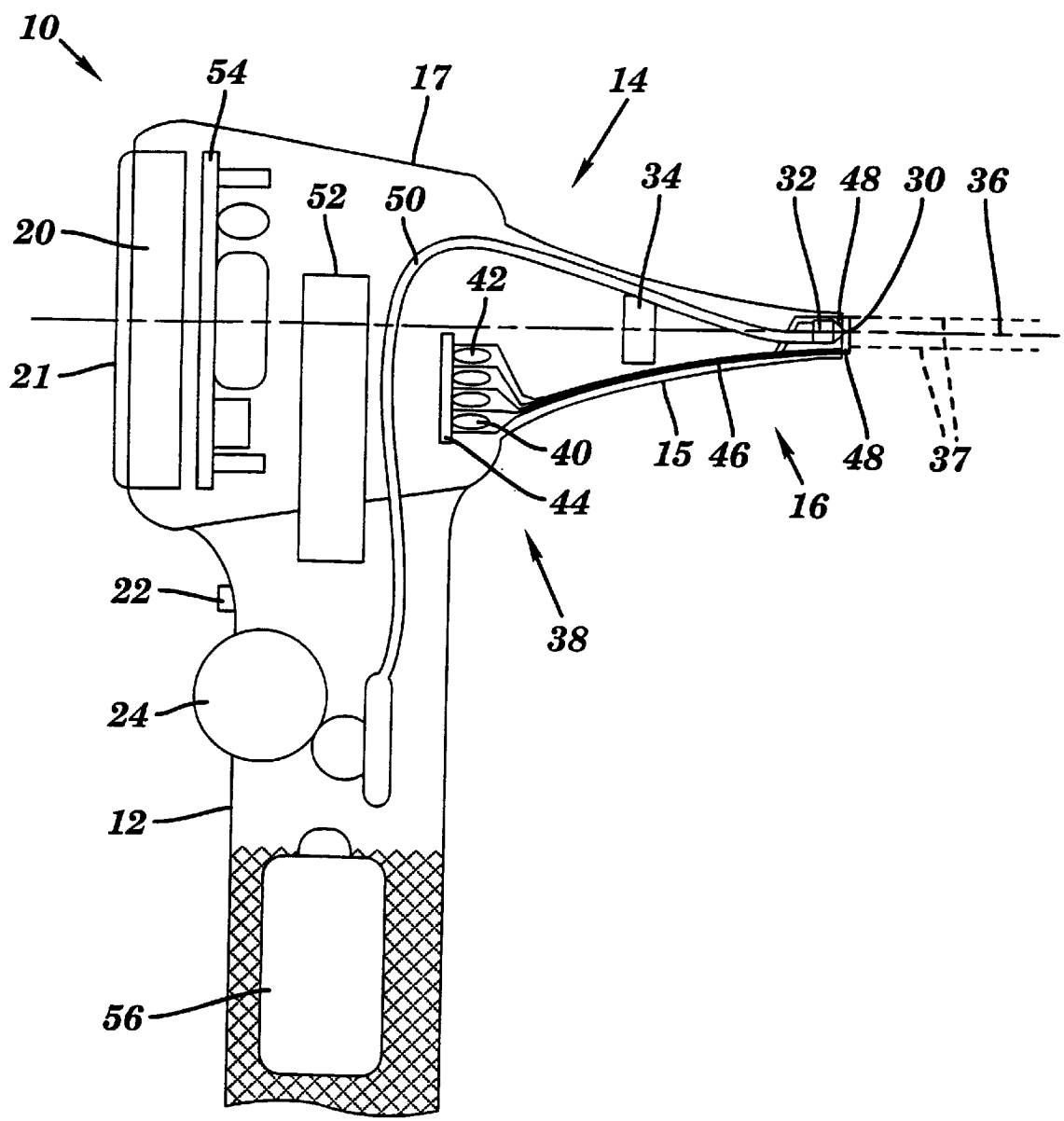
FIG. 2 is an enlarged, broken-away elevational view of a portion of the instrument of FIG. 1.
Figure 3:
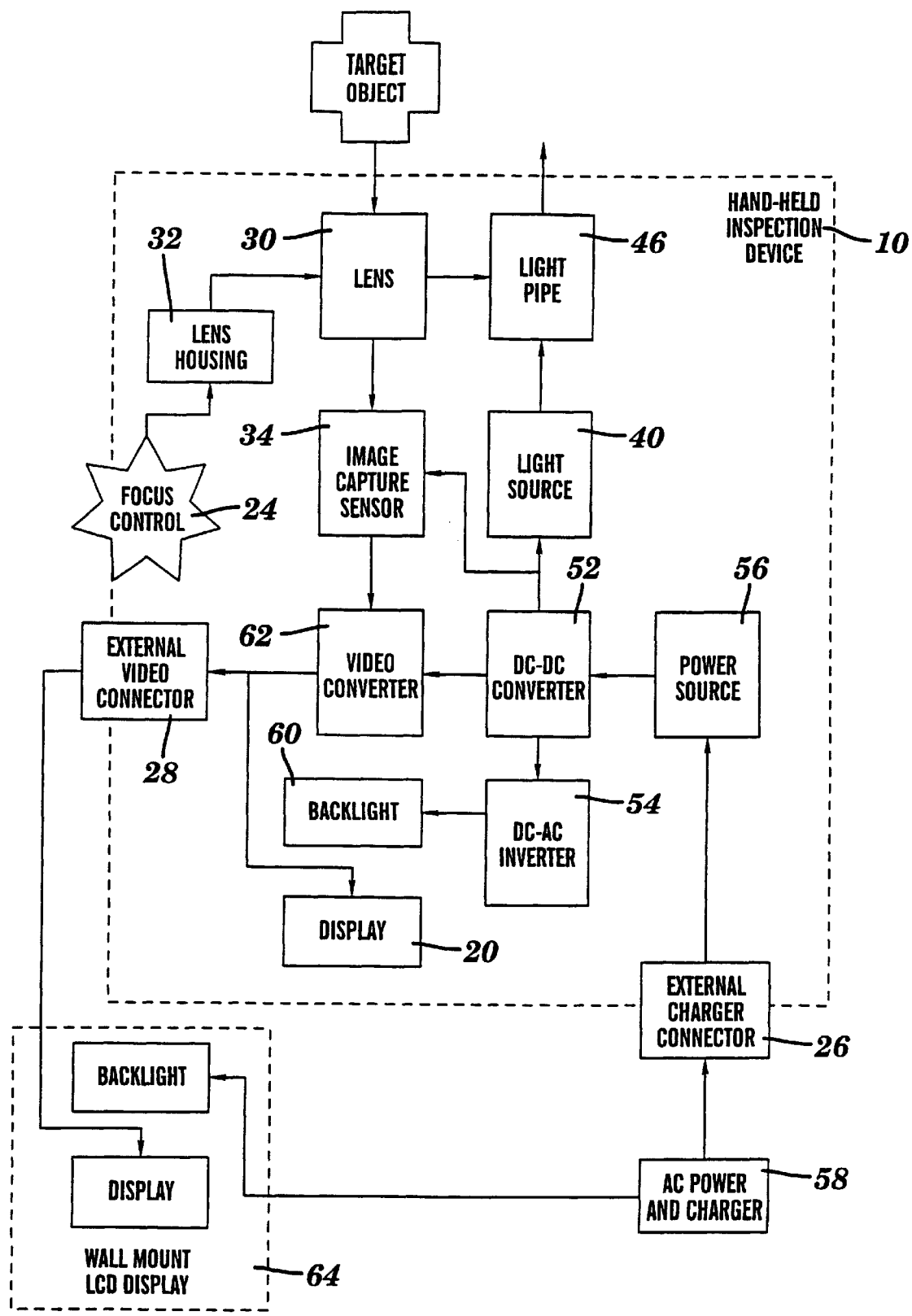
FIG. 3 is a block diagram of the componentry of the present invention.

As shown in FIGS. 1–3, the present invention includes a dental/medical instrument 10 for use in diagnostic and related patient inspection/examination. The device includes a body 12 including an integral speculum 14 with a video image capture device or camera 16, a power supply and a video display 20. These components, in addition to user actuatable controls including a power switch 22 and image focus control 24, are disposed integrally with the body 12. Body 12 is adapted for convenient engagement and manipulation by a user's hand. The present invention thus provides a unitary, hand-held device capable of illuminating and capturing an image of a patient, and displaying the image.

As used herein, the term "light" is defined as electromagnetic energy within the range of frequencies or wavelengths extending from infrared to ultraviolet radiation and including visible light.

Turning now to the Figures in greater detail, as shown in FIG. 1, dental/medical instrument 10 comprises a unitary body 12 including a manually engagable grip portion 13 and a speculum 14. The speculum 14 be either physically housed within the body 12 or integrally fastened to or fabricated as part of the body 12. As also shown, base 12 includes an integral video display 20 as well as user actuatable controls including a power or on/off switch 22 and a focus control 24. The instrument 10 also includes integral battery recharging contacts 26 and an external video port 28, which will be discussed hereinbelow.

Turning now to FIG. 2, the image capture device 16 is disposed within the speculum 14 of the instrument 10. The image capture device 16 includes a lens 30 disposed within a lens housing 32, and an image sensor 34. As also shown, lens 30, housing 32 and sensor 34 are all disposed in image capturing alignment with one another to capture images disposed along an axis of examination 36. Instrument 10 also includes an internal light source 38 which includes a light generator 40 such as an array of light emitting diodes (LEDs) 42 disposed on a printed circuit board 44. Light source 38 further includes an optical coupling such as a light pipe or fiber-optic coupling 46 optically coupled to a light outlet 48. As shown, light outlet 48 preferably includes distal or terminal portions of the light pipe 46 which are splayed for disposition about the periphery of lens housing 32. As shown, each of these terminal portions extends substantially parallel to axis of examination 36 to emit light along light emission axes 37 which are substantially parallel or slightly convergent towards axis 36. In this manner outlet 48 emits light nominally coaxial with axis of examination 36.

Although light generator 40 preferably includes LEDs 42 as shown, any suitable light generation means, such as miniature incandescent bulbs, compact florescent lighting, or one or more lasers may be utilized. Image sensor 34 may be any suitable miniature video image capture device known to those skilled in the art, such as, for example form factor video cameras, or semiconductor chip mounted CCD devices. As also shown, a focus control switch 24, such as a user actuatable thumb wheel as shown, is operatively coupled by cable 50 to the lens housing 32 to effect focus the image captured by image sensor 34. In the embodiment shown, focus control 24 includes a mechanical gear-type control which actuates cable 50 to effect focusing movement of the lens 30 relative to sensor 34 in a known manner.

The instrument power supply includes a DC-DC converter 52 electrically coupled to a DC-AC power inverter 54. Power inverter 54 is, in turn, electrically coupled to video display 20. In a preferred embodiment, as shown, instrument 10 includes an internal power source such as a rechargeable or non-rechargeable battery 56 electrically coupled to DC-DC converter 52. Video display 20 is preferably a color liquid crystal display (LCD) monitor disposed integrally within body 12 in spaced relation to lens housing 32 along axis of examination 36 at a proximal end of speculum 14. An example of a suitable display 20 is known as a 1.8 inch high density LCD display available from Prime View International Co., Ltd., Model number is P18BD1. Moreover, in a preferred embodiment, the substantially planar screen portion 21 of display 20 is disposed substantially orthogonally to the axis of examination 36. Such placement of monitor 20 advantageously places a displayed image generally within a natural line of sight of speculum 14 defined by axis of examination 36. This use of the integral video display 20 advantageously provides an integrated one-piece instrument 10 which enables a user to view an image which moves in a natural and intuitive manner in response to movement of the instrument 10 by a user. Advantageously, this action facilitates proper use with little or no training to generally enable a user to operate the instrument with greater tactile sensitivity than prior devices which utilize discreet video displays located remotely from the image sensing device. The use of an integral display 20 disposed within the axis of examination 36 also advantageously tends to improve the efficiency of the examination procedure by enabling the user to look in a single direction for viewing the image captured on the monitor 20, the instrument 10 and the patient while manipulating the instrument 10. This aspect thus provides improved ergonomics to enable manipulation of the instrument 10 with greater accuracy than prior art devices which generally require the user to manipulate the device while looking away from the patient to view a remote monitor.

Turning now to FIG. 3, a rechargeable power source 56 is electrically coupled to contacts 26 which, in turn, are adapted for connection to an AC power source 58. Internal power source 56 is coupled to DC-DC converter 52 which, as shown, is coupled to a light generator 40 which is coupled to light pipe 46. DC-DC converter 52 is also coupled to the DC-AC inverter 54 to supply power to a backlight 60 of video display 20. As further shown, DC-DC converter 52 provides power to a video converter 62 which provides an electronic image signal to the display 20 as well as to external video port 28. Port 28 may be coupled a remote video display 64. As also shown, lens 30 is optically coupled to sensor 34 which is, in turn, electronically coupled to the video converter 62. Focus control 24 is electrically and/or mechanically coupled to the lens 30.

Figure 4:
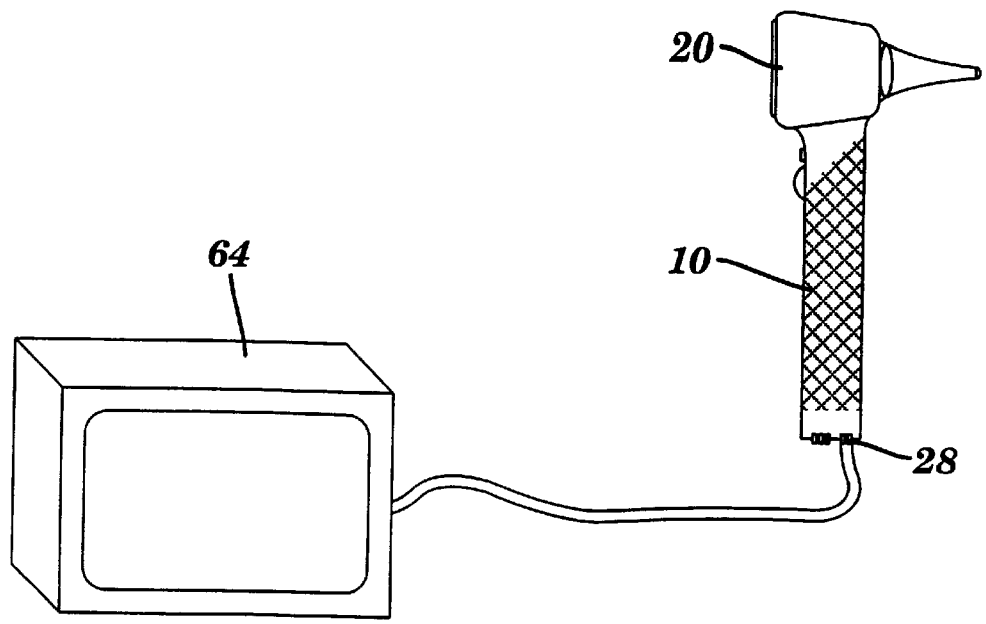
FIG. 4 is a perspective view of the instrument of FIG. 1 including an additional component of the present invention.

Turning now to FIG. 4, in a preferred embodiment inspection device 10 is adapted for being coupled by its external video port 58 to a remote monitor 64. The remote monitor 64 may comprise a LCD display, television monitor, and the like, and is preferably wall mounted or movably mounted to enable a patient to view captured images in real time as the dentist or physician views the captured images on the integral display 20. This aspect of the present invention thus provides the user with a useful tool for explaining and or describing the examination process to the patient. Moreover, the image may be recorded by connecting the video output to a suitable image recorder such as a computer or VCR or other recording device.

Figure 5:
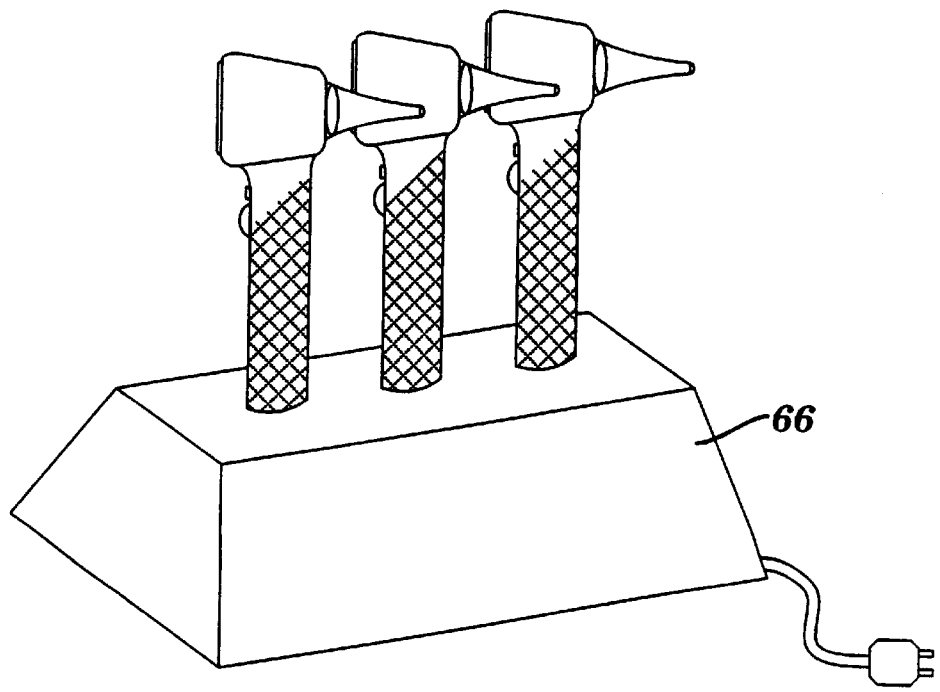
FIG. 5 is a perspective view of a plurality of instruments of FIG. 1 disposed in an optional charging device.

As shown in FIG. 5, an AC powered recharging base 66 may be utilized to receive one or more instruments 10 for recharging power source 56 by coupling external charger contacts 26 (FIG. 1) to AC power supply 58 (FIG. 3).

Having thus described the invention, what is claimed is:

1. A portable unitary hand-held otoscope for aural examination, comprising:

a body having a pistol-grip adapted for engagement by a user's hand;

said body including a rigid frusto-conical speculum disposed thereon, said speculum having a distal tip opening disposed along an axis of examination, said speculum being sized to allow location of said distal tip opening a predetermined distance within a target ear canal;

an image capture device and a light source, said image capture device and said light source being disposed integrally within said body, to capture an image of the target ear viewed by said image capture device through said distal tip opening; and a substantially planar video display housed within said body, said video display being disposed within said axis of examination in orthogonal relation thereto, to locate a displayed image of the target ear within and orthogonal to said axis of examination.

2. The otoscope of claim 1, further comprising a power supply disposed integrally with said body.

3. The otoscope of claim 2, further comprising a power source disposed integrally with said body.

4. The otoscope of claim 1, wherein said image capture device and said light source are disposed integrally within said speculum.

5. The otoscope of claim 1, wherein said image capture device comprises a lens disposed in optical communication with an image sensor.

6. The otoscope of claim 5, wherein said light source emits light substantially coaxially with a central optical axis of said image capture device.

7. The otoscope of claim 6, wherein said light source further comprises a light emitting diode.

8. The otoscope of claim 1, further comprising a user actuatable power switch disposed integrally on said body.

9. The otoscope of claim 1, further comprising a power supply disposed integrally within said body.

10. The otoscope of claim 9, wherein said power supply is adapted for being coupled with an external power source.

11. The otoscope of claim 10, wherein said power supply further comprises charging circuitry adapted to recharge rechargeable batteries disposed integrally with said body.

12. The otoscope of claim 11, wherein said charging circuitry further comprises contacts disposed externally on said body, said contacts adapted for power coupling contact with an external power source when said body is received within a charger.

13. The otoscope of claim 1, further comprising video circuitry adapted to couple said image capture device with said video display.

14. The otoscope of claim 13, wherein said video circuitry further comprises an external port disposed on said body, said external port adapted to couple with an external video display.

15. The otoscope of claim 14, further comprising an external video display.

16. The otoscope of claim 1, wherein said image capture device further comprises an image recorder.

17. The otoscope of claim 1, further comprising an image recorder.

18. The otoscope of claim 1, further comprising a focus control switch disposed on said body.

19. A portable hand-held otoscope for aural examination, comprising:

a body having a pistol-grip adapted for engagement by a user's hand;
said body including a rigid frusto-conical speculum disposed thereon, said speculum having a distal tip opening disposed along an axis of examination, said speculum being sized to allow location of said distal tip opening a predetermined distance within a target ear canal;
an image capture device disposed integrally within said body, said image capture device having a central optical axis;
a light source disposed integrally within said body, said light source being adapted to emit light along at least one light emission axis disposed substantially parallel to said central optical axis; and
a video display housed within said body, said video display being disposed within said axis of examination in orthogonal relation thereto, said video display being coupled with said image capture device to display an image captured thereby.

20. A method of examining a patient comprising the steps of:

(a) utilizing a portable hand-held otoscope including:
a body having a pistol-grip adapted for engagement by a user's hand;
said body including a rigid speculum disposed thereon;
an image capture device;
a light source;
said image capture device and said light source being disposed integrally with said body; and
a substantially planar video display housed within said body, said video display being disposed within an axis of examination in orthogonal relation thereto; and (b) manipulating the instrument relative to a patient while the user simultaneously faces both the patient and the video display.

21. The method of claim 20, further comprising the step of:

(c) enabling the patient to view the image on a remote display coupled to the instrument.

22. The method of claim 21, further comprising the step of:

(d) recording the image on an image recorder.

23. A portable hand-held otoscope comprising:

a body having a pistol-grip adapted for engagement by a user's hand;
said body including a rigid frusto-conical speculum disposed thereon; said speculum having a distal tip opening disposed along an axis of examination, said speculum being sized to allow location of said distal tip opening a predetermined distance within a target ear canal;
a lens and a light outlet, said lens and said light outlet being disposed integrally within said body; and
a substantially planar video display disposed integrally with said body said video display being disposed within an axis of examination in orthogonal relation thereto.

* * * * *